(12) United States Patent
Garvey et al.

(10) Patent No.: US 10,631,881 B2
(45) Date of Patent: Apr. 28, 2020

(54) PLATING DEPTH GAUGE AND COUNTERSINK INSTRUMENT

(71) Applicant: Flower Orthopedics Corporation, Horsham, PA (US)

(72) Inventors: Brian Garvey, Media, PA (US); Kevin Rzasa, Upper Chichester, PA (US); Oliver Burckhardt, Philadelphia, PA (US); John Levin, West Palm Beach, FL (US)

(73) Assignee: Flower Orthopedics Corporation, Horsham, PA (US)

( * ) Notice: Subject to any disclaimer, the term of this patent is extended or adjusted under 35 U.S.C. 154(b) by 43 days.

(21) Appl. No.: 15/454,698

(22) Filed: Mar. 9, 2017

(65) Prior Publication Data

US 2018/0256277 A1   Sep. 13, 2018

(51) Int. Cl.
*A61B 17/16* (2006.01)
*A61B 90/00* (2016.01)

(52) U.S. Cl.
CPC ...... *A61B 17/1659* (2013.01); *A61B 17/1615* (2013.01); *A61B 2090/062* (2016.02)

(58) Field of Classification Search
CPC ............... A61B 17/1659; A61B 90/06; A61B 2090/062; A61B 17/1615
USPC .......................................................... 606/102
See application file for complete search history.

(56) References Cited

U.S. PATENT DOCUMENTS

| 8,728,088 | B2 * | 5/2014 | Lebeau | A61B 90/06 606/102 |
| 2013/0096565 | A1 * | 4/2013 | Fritzinger | A61B 90/06 606/102 |
| 2014/0343561 | A1 * | 11/2014 | Penzimer | A61B 17/7074 606/102 |
| 2015/0133944 | A1 * | 5/2015 | Kortenbach | A61B 90/06 606/102 |

* cited by examiner

*Primary Examiner* — Si Ming Ku
(74) *Attorney, Agent, or Firm* — Riverside Law LLP

(57) ABSTRACT

The present invention relates to a multi-tool or multi-purpose device comprising a counter sink and a depth gauge. In one aspect, the invention provides a method of determining the necessary length of a screw to be implanted into bone. Also provided herein are sterile kits comprising single-use instrumentation for use in orthopedic procedures.

19 Claims, 4 Drawing Sheets

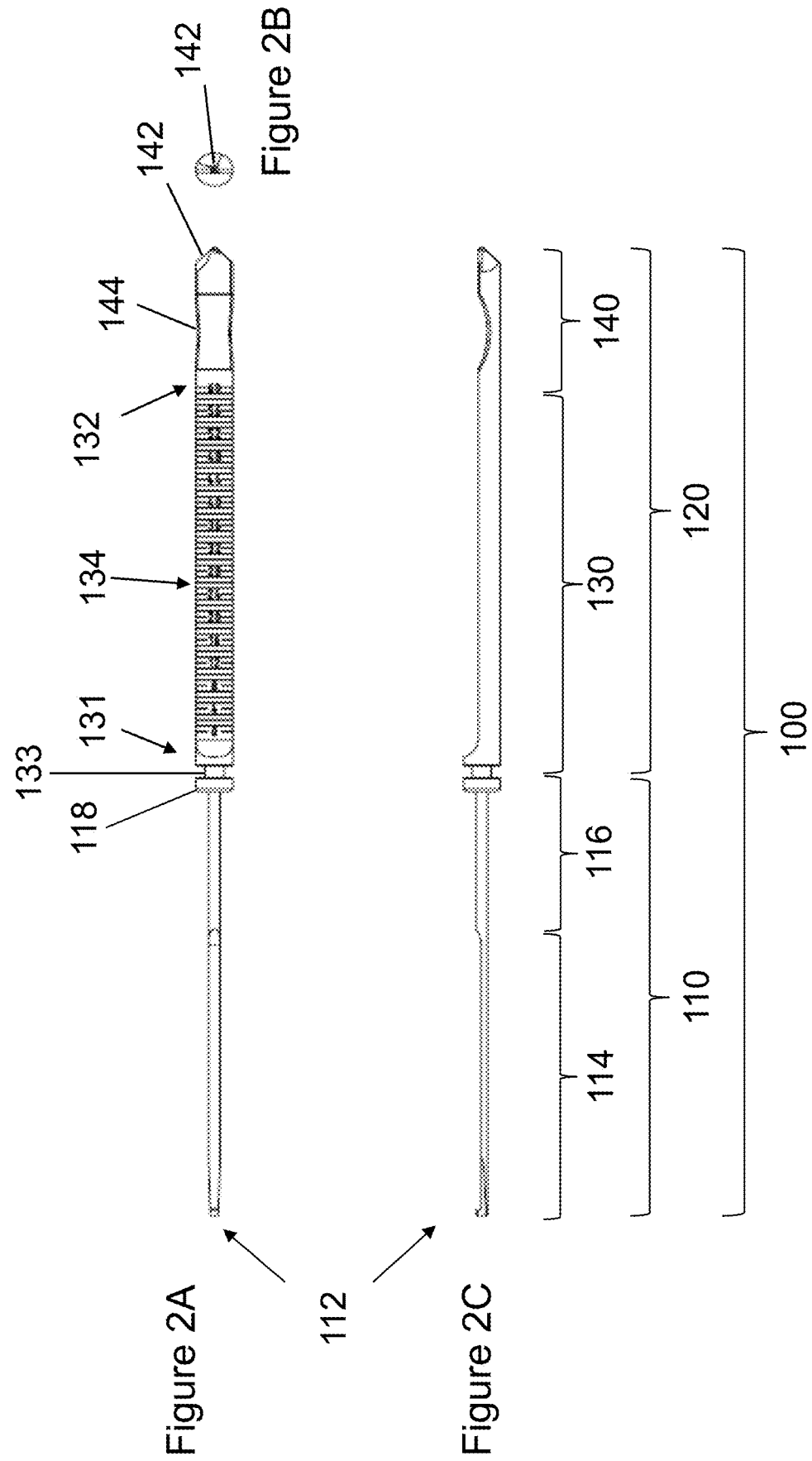

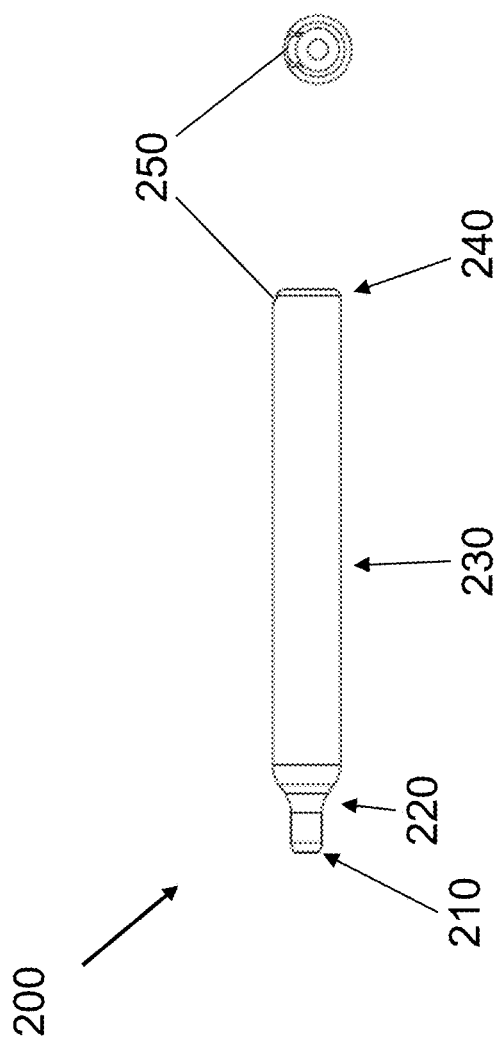

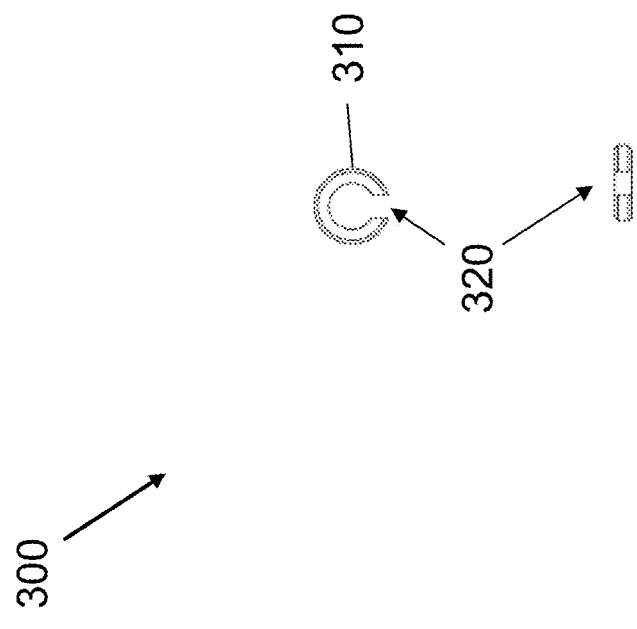

PLATING DEPTH GAUGE AND COUNTERSINK INSTRUMENT

BACKGROUND OF THE INVENTION

During certain orthopedic procedures, it is necessary to use a countersink to prepare the bone for the seating of a screw. Further, in certain instances, it is desired for the surgeon to know the required length of the screw to be inserted into the bone. Traditionally, these two steps are performed by separate devices, which increases the risk of adverse effects as each device is separately applied and removed.

Thus, there is a need in the art for improved devices for orthopedic procedures. The present invention satisfies this unmet need.

SUMMARY OF THE INVENTION

In one embodiment, the device of the present invention relates to a multi-purpose device for use in an orthopedic procedure, including a shaft having a proximal end and distal end. In one embodiment, the shaft includes a hook positioned at the proximal end and a countersink positioned at the distal end, a casing through which the shaft is positioned, and a ring, whereby the ring attaches to the shaft, positioned on a region of the shaft that is internal to the casing.

In one embodiment, the hook of the shaft includes a portion with a central axis that is not parallel to the central axis of the shaft.

In one embodiment, the countersink portion of the device includes one or more cutting flutes.

In one embodiment, the shaft of the device includes a graduated portion including at least one graduation marking along the shaft wherein at least a portion of the graduated portion of the shaft is visible from the outer surface of the casing.

In one embodiment, the graduated portion includes a numbering scale. In one embodiment, the numbering scale has units in inches. In one embodiment, the numbering scale has metric units, wherein the metric units are in millimeters.

In one embodiment, the shaft of the device is constructed from a biocompatible material including stainless steel, aluminum, titanium alloy, cobalt alloy, titanium ceramic, aluminum oxide, zirconia, silicone, and plastic.

In one embodiment, the casing of the device is coaxial to and exterior to the shaft. In one embodiment, the casing is made of a biocompatible material selected from the group consisting of stainless steel, aluminum, titanium alloy, cobalt alloy, titanium ceramic, aluminum oxide, zirconia, silicone, and plastic. In one embodiment, the casing comprises a viewing window.

In one embodiment, the ring of the device includes one or more cutaway regions. In one embodiment, the ring is made of a biocompatible material selected from the group consisting of stainless steel, aluminum, titanium alloy, cobalt alloy, titanium ceramic, aluminum oxide, zirconia, silicone, and plastic. In one embodiment, the hook, graduated portion, and countersink of the shaft are constructed from a single material. In one embodiment, the hook, graduated portion, and countersink of the shaft are constructed from a composite of materials.

In one embodiment, the present invention provides a method of determining the necessary length of a screw to be inserted into a bone during an orthopedic procedure, including inserting the proximal end of the device of claim 1 into a predrilled hole into bone, observing a graduated marking of a graduated portion of the device of claim 1 through a window in the casing of the device, and determining the length of the screw based on the observed depth of the shaft inserted into the bone.

In one embodiment, the invention relates to a method of using the device of the invention, wherein the device includes at least one graduation marking along the shaft where at least a portion of the shaft is visible from the outer surface, and wherein measuring the depth of the shaft within the bone comprises identifying a graduation marking visible within the window in the casing of the device. In one embodiment, the necessary length of the screw is equal to the observed depth of the shaft.

In one embodiment the present invention provides a method of placing a screw using the device of the invention wherein the device comprises a hook and a countersink of the same device.

In one embodiment, the present invention provides a method of preparing a bone for placement of a screw using the device of the invention, including the following steps: 1) determining the appropriate hole depth and screw length using the hook and graduated portion of the device; and 2) preparing the site of interest on the bone for a screw using the countersink portion of the device.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

FIG. 1, comprising FIG. 1A illustrates a top view of an exemplary device of the invention. FIG. 1B illustrates a cross-sectional view of an exemplary device of the invention.

FIG. 2, comprising FIG. 2A through FIG. 2C, is an orthogonal drawing illustrating an exemplary central body of the device. FIG. 2A illustrates a top view of an exemplary device of the invention. FIG. 2B illustrates an end view of the distal end of an exemplary device of the invention. FIG. 2C illustrates a side view of an exemplary device of the invention.

FIG. 3, comprising FIG. 3A and FIG. 3B, is a two-view orthogonal drawing illustrating an exemplary casing of the device of the invention. FIG. 3A illustrates a side view of an exemplary casing of the device. FIG. 3B illustrates an end view of the distal end of an exemplary casing of the device of the invention.

FIG. 4, comprising FIG. 4A and FIG. 4B, is a two-view orthogonal drawing illustrating an exemplary stabilizing ring of the device. FIG. 4A is a side view of an exemplary ring of the device. FIG. 4B is a top view of an exemplary ring of the device.

DETAILED DESCRIPTION

Definitions

Figures 1A, 1B:
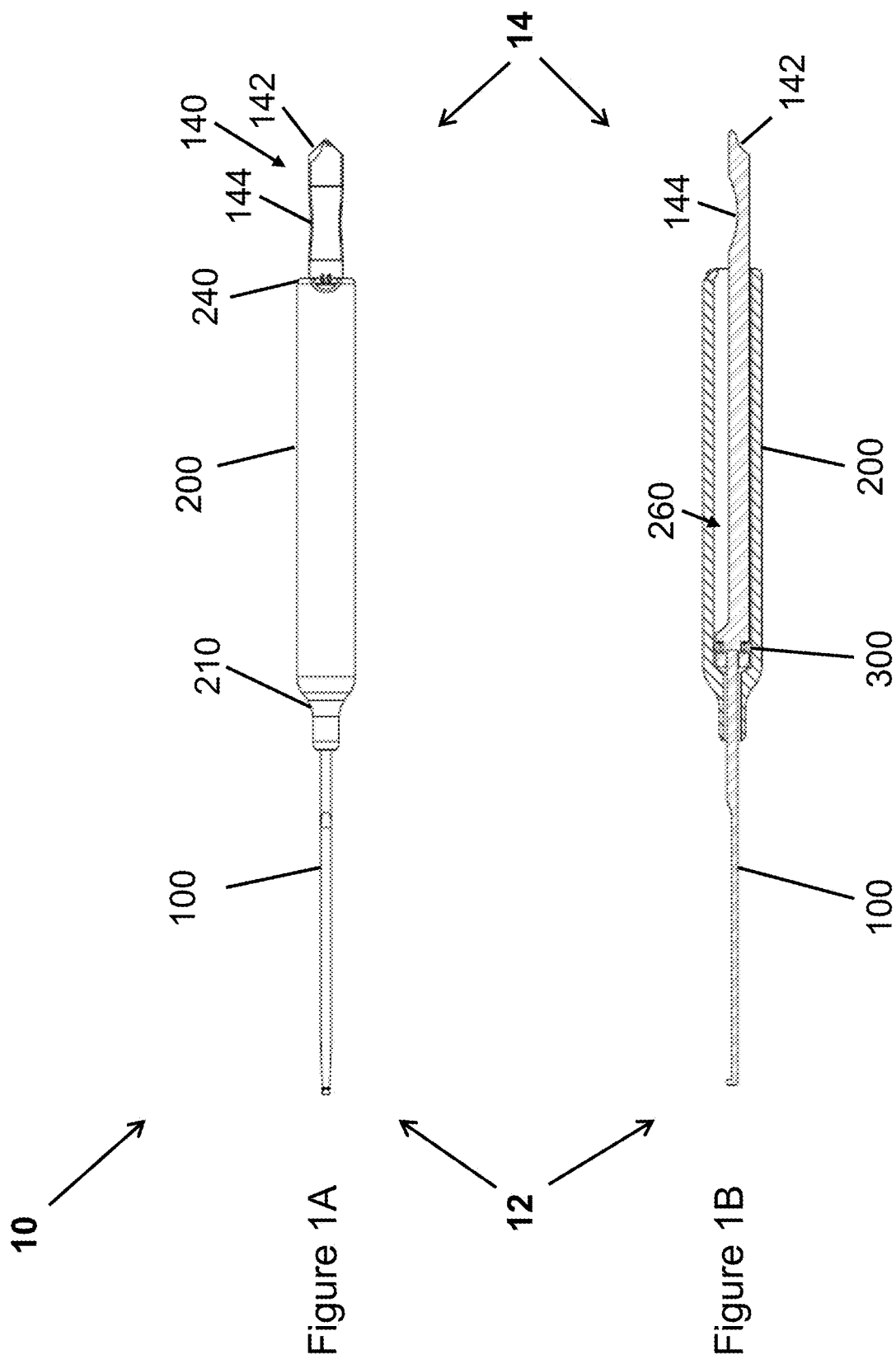
FIG. 1A and FIG. 1B, is a schematic illustrating an exemplary device of the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to a multi-tool device comprising a countersink and a depth gauge. The device may be used in a variety of orthopedic surgical procedures, including but not limited to procedures to repair a broken bone or the fusion of two or more bones together.

In one aspect, the device comprises a countersink, which may be used to prepare a target site on a bone for the subsequent seating of a screw. For example, the countersink of the device is used to provide a countersunk recess in the bone, such that the head of the screw upon insertion either sits below the bone surface, is flush with the bone surface, or is at least partially embedded in the bone surface.

In one aspect, the device comprises a depth gauge to determine the necessary length of a screw to be inserted at the target site. For example, in certain embodiments, the device is used to measure the depth to which a hook is inserted into the target site, which thereby provides a measurement of the necessary screw length.

In certain embodiments, the device is provided in a sterile package. For example, the sterile package may comprise one or more of the devices described herein. In certain embodiments, the sterile package comprises one or more of the devices described herein, together with one or more instruments that may be necessary to perform the desired orthopedic procedure. The sterile package allows for immediate use of the device and other instruments without the need for pre-processing. In certain aspects, the device and other instruments are configured for single-use applications.

Device

FIG. 1 depicts an exemplary device 10 of the present invention. Device 10 comprises an elongated shaft 100, a casing 200, and a stabilizing ring 300. Shaft 100 comprises a proximal end 12 and a distal end 14. In certain embodiments, device 10 may have a total length of about 10 mm to about 1000 mm. For example, in certain embodiments, device 10 has a total length of about 10 mm, 20 mm, 30 mm, 40 mm, 50 mm, 60 mm, 70 mm, 80 mm, 90 mm, 100 mm, 200 mm, 250 mm, 300 mm, 400 mm, 500 mm, 600 mm, 700 mm, 800 mm, 900 mm, or 1000 mm. Device 10 may be manufactured from any suitable material such as any biocompatible or non-bioreactive materials, including but not limited to stainless steel, aluminum, titanium alloy, cobalt alloy, titanium ceramic, aluminum oxide, zirconia, silicone, polymers, plastic, and the like.

Referring now to FIG. 2, shaft 100 comprises proximal shaft 110 and distal shaft 120. Proximal shaft 110 comprises hook 112, narrow portion 114, and wide portion 116. Proximal shaft 110 is defined by hook 112 and stop 118. Hook 112 may be used for engaging the far cortex of a bi-cortically drilled hole. Hook 112 comprises a major diameter larger than the adjacent narrow portion 114 of shaft 100. In certain embodiments, the primary axis of hook 112 is not parallel to the primary axis of shaft 100. Narrow portion 114 can have a diameter of about 1 mm, 2 mm, 3 mm, 4 mm, 5 mm, 6 mm, 7 mm, 8 mm, 9 mm, or 10 mm. Wide portion 116 has a diameter of about 1 mm, 2 mm, 3 mm, 4 mm, 5 mm, 10 mm, or 50 mm. Hook 112, narrow portion 114, and wide portion 116 of shaft 100 may be constructed from a standard, stiff, rigid metal or material as commonly used by those skilled in the art. For example, hook 112, narrow portion 114, and wide portion 116 of proximal shaft 110 may be constructed from a metallic material that is strong enough to penetrate the surface of bone and the interior of bone. Hook 112, narrow portion 114, and wide portion 116 of proximal shaft 110 can be configured to be drilled, screwed, or twisted into bone using standard techniques understood in the art. In one embodiment, hook 112, narrow portion 114, and wide portion 116 of proximal shaft 110 and are constructed from one continuous body of material. In one embodiment, hook 112, narrow portion 114, and wide portion 116 are formed from separate bodies of material and are rigidly joined together to form proximal shaft 110 by means known to one skilled in the art, for example welding, soldering, sintering, riveting, and the like.

Distal shaft 120 comprises stop 118, groove 133, graduated portion 130, and countersink 140. Distal shaft 120 is defined at a proximal end by stop 118 and at a distal end by countersink 140. Graduated portion 130 is defined by proximal boundary 131 and distal boundary 132. Graduated portion 130 is a cut away portion of distal shaft 120 comprising a cylindrical shape with a semi-circular cross-section. Graduated portion 130 comprises calibrated laser markings measured relative to hook 112. Countersink 140 includes curvature 144 used to provide improved ergonomics of handling and actuating the device, and one or more cutting flutes 142 used to prepare the bone for the subsequent seating of a screw. Cutting flutes 142 may have a curved cross-sectional shape, a circular cross-sectional shape, or a semi-circular cross-sectional shape, as would be understood by those skilled in the art for generating a recess into the bone surface. In one embodiment, cutting flutes 142 are constructed from a metal or other hard, rigid material that is strong enough for the leading edge to cut, scrape away, or otherwise remove the portion of the bone when device 10 is actuated.

In one embodiment, proximal shaft 110 and distal shaft 120 are formed from a continuous body of material. In one embodiment, proximal shaft 110 and distal shaft 120 are formed from two distinct bodies of material and joined together by a means known to one skilled in the art, for example welding, soldering, sintering, riveting, and the like. As contemplated herein, device 10 may be actuated by rotational movement, with or without forward pressure, thereby causing cutting flutes 142 to engage and remove a portion of the bone to form the desired recess. As contemplated herein, countersink 140 may be used to form an appropriately sized and shaped recess in the bone to allow for a subsequently inserted screw head to be at least partially embedded in the bone, be flush with or sit below the bone surface.

In certain embodiments, countersink 140 has a tip geometry that accommodates the particular geometry of the screw head to be used. For example, in certain embodiments, the geometry of countersink 140 is angled to produce a recess with a defined angle to match the angle of the screw head being used. However, the geometry of countersink 140 may or may not be identical to the undersurface of the screw head. Further, countersink 140 is appropriate for accommodating the insertion of various screw heads with different head diameters.

Referring now to FIG. 3, casing 200 comprising a narrow portion at proximal end 210, a billowing curvature 220, a wide portion 230, a distal end 240 with a beveled edge, and a viewing window 250. In one embodiment, viewing window 250 is formed by removing a certain portion of material from distal end 240. The approximate average outer diameter of the narrow portion of proximal end 210 is about 3 mm, 10 mm, 20 mm, or 30 mm. The approximate average outer diameter of wide portion 230 is about 5 mm, 10 mm, 20 mm, 30 mm, 40 mm, or 50 mm. In one embodiment, curvature 220 of casing 200 is formed by any suitable means known by one skilled in the art including milling incremental graduated diameters ranging from the outer diameter of proximal end 210 to the outer diameter of wide portion 230. Casing 200 comprises a hollow bore 260 (visible in FIG. 1B) that accommodates shaft 100 and ring 300. Casing 200 may be manufactured from any suitable material such as any biocompatible or non-bioreactive materials, including but not limited to stainless steel, aluminum, titanium alloy, cobalt alloy, titanium ceramic, aluminum oxide, zirconia, silicone, polymers, plastic, and the like. In one embodiment, the hollow bore 260 of casing 200 is formed by any suitable means known by one skilled in the art including drilling a channel in a solid cylindrical material.

In certain embodiments, casing 200 comprises one or more handling features, such as flats or knurling, that allow for ergonomic use of device 10. For example, the one or more features may allow for ergonomic handing of device 10 and rotation of device 10, for the actuation of countersink 140.

Referring now to FIG. 4, ring 300 comprises circular portion 310 and cutaway 320. Ring 300 is positioned with respect to shaft 100 such that it sits within groove 133. In practice, ring 300 is used to provide axial stability and sliding friction to shaft 100 within casing 200. Ring 300 can be manufactured from any suitable material such as any biocompatible or non-bioreactive materials, including but not limited to stainless steel, aluminum, titanium alloy, cobalt alloy, titanium ceramic, aluminum oxide, zirconia, silicone, polymers, plastic, and the like.

Device 10 may be used for measurement of the screw length needed for a desired application. For example, as shown in FIG. 2, shaft 100 of device 10 may include a graduated portion 130 at least partially along its length. Graduated portion 130 may be at least partially exposed to allow for visual observation of graduation through viewing window 250 in casing 200.

In one embodiment, graduated portion 130 comprises measurement graduations, such as a numbering scale 134, to allow for measurement of the position of hook 112 extending within a drilled hole in the bone surface. As contemplated herein, this measurement of the hook position may be used to determine the necessary screw length for subsequent insertion into the bone.

For example, in one embodiment, numbering scale 134 provides a measurement of the depth of hook 112 internal to the bone, providing the desired length of the screw for insertion. Numbering scale 134 may have markings in millimeters, centimeters, inches, arbitrary units, or any other suitable graduation for determining length measurement or positioning.

Methods

The present invention also provides a method for guiding placement of a countersunk recess in a target site of bone. In certain embodiments, the method comprises inserting hook 112 and narrow portion 110 of shaft 100 into a target site of bone, where the target site is the site in which a screw will eventually be inserted during a procedure.

Once hook 112 is inserted into the target site of bone, shaft 100 slides independent of casing 200 until hook 112 engages distal cortical surface of bone. In another aspect, the method comprises gripping casing 200 to push hook 112 into a target site of bone to press hook 112 against the distal cortical surface of bone, wherein further pushing slides casing 200 down shaft 100 until proximal end 210 of casing 200 meets the outer bone surface. In certain embodiments, the insertion depth of hook 112 can be determined by observing the numbered laser mark of numbering scale 134 positioned in viewing window 250 indicating the depth of tip of hook 112 relative to the surface of a target site of bone. In certain embodiments, device 10 is actuated to produce a countersunk recess in bone, thereby preparing the bone for the subsequent seating of a screw to sit flush, below the bone surface, or otherwise be at least partially embedded into the bone surface. For example, after the desired depth of the drilled hole in the target bone has been achieved, wherein hook 112 has engaged the distal cortex of bone following drilling of a hole, for example a bi-cortical hole, cutting flutes 142 of countersink 140 can be placed in direct contact with the target site of bone. Once in contact with the surface of bone, device 10 is actuated, for example by rotating, turning, or twisting, thereby allowing cutting flutes 142 to form the desired shape and depth recess to produce a countersunk recess for the head of a screw. It should be appreciated that accurate measurement of necessary screw length may or may not be predicated on the use of countersink 140.

The present invention also provides a method of measuring the length of a screw required for a desired surgical application. For example, the method utilizes device 10 for measuring the depth that hook 112 is inserted into a target site of a bone. In one embodiment, numbering scale 134 has a plurality of graduation markings indicative of the length of the screw required, as measured from the distal boundary 132 of the graduated portion 130. As a result of measuring the depth of hook 112 by visualizing position of numbering scale 134 of graduated portion 130 through viewing window 250, a proper screw length may be determined for subsequent insertion.

Kits

In one aspect, the present invention provides an implant kit comprising instrumentation to place a bone implant during an orthopedic procedure. In certain embodiments, the implant kit is a sterile packaged kit. In certain embodiments, the one or more instruments of the implant kit are sterile and contained in one or more individual sterile packages within the kit. The sterile implant kit described herein is thus immediately ready for surgical application upon removal of the instruments from their respective packages without the need for pre-operation cleaning, sterilizing, or other processing. In certain aspects, the one or more instruments of the implant kit are single-use instruments. For example, in one embodiment, the one or more instruments of the implant kit are sterile and disposable. In another embodiment, the one or more instruments of the implant kit are repackaged after use, where, in certain embodiments, the one or more instruments may be reprocessed for future use. In one embodiment, the instruments may be provided in one or more blister packaging. Each blister may comprise a plastic container (e.g., PETG) component and a lid (e.g., Tyvek) component.

In certain embodiments, the implant kit comprises a countersink-depth gauge multi-tool device, such as device 10 of FIG. 1. In certain embodiments, the implant kit may optionally include other instruments, such as and without limitation, one or more implantable screws, one or more implantable bone plates, one or more plating screws, one or more screw drivers, one or more screw depth gauges, one or more preliminary fixation devices, one or more drill bits, and/or one or more drill guides. For example, in one embodiment, the implant kit comprises one or more implantable screws, which may be cannulated or solid screws, or a combination thereof. In one embodiment, the implant kit comprises one or more bone plates, including any size or geometry of plate which may be necessary for the desired application. The one or more bone plates may accept locking screws, non-locking screws, or a combination thereof. In one embodiment, the implant kit comprises one or more plating screws. In one embodiment, the implant kit comprises one or more screwdrivers. The one or more screwdrivers may be cannulated, for use with cannulated screws. In one embodiment, the one or more screwdrivers may be solid, for use with solid screws and plating screws. In one embodiment, implant kit comprises at least one cannulated screwdriver and at least one solid screwdriver. In one embodiment, the implant kit comprises one or more solid screw depth gauges, used to measure the length of plating screws to be used with or without a plate. In one embodiment, the implant kit comprises one or more preliminary fixation devices, including, but not limited to k-wires or olive wires, which may be placed through a bone plate to hold the plate in place prior to and during insertion of screws. In one embodiment, the implant kit comprises one or more drill bits, used to create a pilot hole for subsequent screw insertion. In certain embodiments, the one or more drill bits are cannulated for use with cannulated screws. In certain embodiments, the one or more drill bits are solid for use with solid screws. In one embodiment, the implant kit comprises at least one cannulated drill bit and one or more solid drill bit. In one embodiment, the implant kit comprises one or more drill guides. The one or more drill guides may be used to center a pilot hole within the bone plate when plating screws are used.

Accordingly, the implant kit may include some or all instrumentation required to place an implant construct for a particular surgical procedure. For example, in one embodiment, the kit comprises any combination of instrumentation for implantation of a cannulated screw, including a countersink-depth gauge multi-tool device, at least one cannulated screwdriver, at least one at least one cannulated drill bit and at least one cannulated screw. In another embodiment, the implant kit comprises any combination of instrumentation for implantation of a bone plate, including a countersink-depth gauge multi-tool device, at least one solid screwdriver, at least one preliminary fixation device, at least one solid drill bit, at least one drill guide and at least one bone plate. In another embodiment, the implant kit comprises any combination of instrumentation for implantation of both a bone plate and screw, where the sterile kit comprises a countersink-depth gauge multi-tool device, at least one screwdriver, at least one preliminary fixation device, at least one drill bit, at least one drill guide, at least one screw and at least one bone plate.

In certain embodiments, the implant kit is custom-configured with regard to size and geometry of the appropriate implant (e.g., bone plate, screw) being used. In one embodiment, the kit is configured for a specific size of screw or bone plate. In an alternative embodiment, the kit comprises instrumentation that may be necessary for various sizes of screws or bone plates, or multiple sized screws and/or bone plates.

In certain embodiments, the kit comprises instructional material. Instructional material may include a publication, a recording, a diagram, or any other medium of expression which can be used to communicate the usefulness of any of the devices or implant kits described herein. The instructional material may also include description of one or more steps to perform any of the methods described herein. The instructional material of the kit may, for example, be affixed to a package which contains one or more instruments which may be necessary for the desired procedure. Alternatively, the instructional material may be shipped separately from the package, or may be available electronically, such as accessible from the Internet, or any downloadable electronic document file format.

Still further, the present invention includes a method of providing a sterile implant kit as described herein. In certain embodiments, the method comprises receiving a request for one or more instruments for use in a surgical procedure. In certain embodiments, the method comprises a customized request for particular instrumentation. In certain embodiments, the method comprises a request for a standardized kit which would contain the one or more instruments. In certain instances, the method comprises gathering the one or more instruments which were requested. In one embodiment, the method comprises processing the one or more instruments. For example, in one embodiment, the one or more instruments are sterilized. Sterilization of the one or more instruments may be conducted by any suitable method known in the art. In one embodiment, the method comprises packaging the one or more instruments. For example, the one or more instruments may be packaged in one or more sterile packages to form a sterile kit.

In one embodiment, the method further comprises providing the assembled kit to a user (i.e., surgeon, surgical staff member, medical assistant or provider, etc.) at a location for utilizing the instrumentation of the kit during the orthopedic procedure. In certain embodiments, the method comprises receiving one or more of the instruments not used during the procedure may be returned to the kit provider. In some embodiments, the returned instruments may result in a credit, discount, refund or other perk associated with the return of an unused instrument. In certain embodiments, the kit provider may use the returned instrumentation to form another kit.

It should be appreciated that the devices and the implant kits described herein may be used for a variety of surgical or non-surgical orthopedic procedures, including, but not limited to internal fixation of fractures, bone reconstruction, fusion of one or more bones or bone fragments, and the like. The procedures may be performed on any bone in the human or vertebrate body, including, but not limited to, scapula, olecranon, humerus, radius, ulna, pelvis, tibia, fibula, clavicle, vertebrae, femur, cranium, hand bones and foot bones. The internal fixation or reconstruction may include compression fractures, intra-articular and/or extra-articular fractures, displaced fractures, osteotomies, non-unions and/or mal-unions. It should be understood that the present disclosure is not limited to a specific bone, fracture type, or surgical application.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A multi-purpose device for use in an orthopedic procedure, comprising:
   a shaft having a proximal end and distal end, wherein the shaft comprises a hook positioned at the proximal end and a countersink positioned at the distal end, wherein the countersink of the shaft comprises one or more cutting flutes;
   a casing through which the shaft is positioned, wherein the casing comprises an outer surface; and
   a ring, wherein the ring attaches to the shaft, positioned on a region of the shaft that is internal to the casing.

2. The device of claim 1, wherein the hook of the shaft comprises a portion with a central axis that is not parallel to the central axis of the shaft.

3. The device of claim 1, wherein the shaft further comprises a graduated portion comprising at least one graduation marking along the shaft wherein at least a portion of the graduated portion of the shaft is visible from the outer surface of the casing.

4. The device of claim 3 wherein the graduated portion comprises a numbering scale.

5. The device of claim 4 wherein the numbering scale has units in inches.

6. The device of claim 4 wherein the numbering scale has metric units, wherein the metric units are in millimeters.

7. The device of claim 1, wherein the shaft comprises a biocompatible material selected from the group consisting of stainless steel, aluminum, titanium alloy, cobalt alloy, titanium ceramic, aluminum oxide, zirconia, silicone, and plastic.

8. The device of claim 1, wherein the casing is coaxial to and exterior to the shaft.

9. The device of claim 1, wherein the casing comprises a biocompatible material selected from the group consisting of stainless steel, aluminum, titanium alloy, cobalt alloy, titanium ceramic, aluminum oxide, zirconia, silicone, and plastic.

10. The device of claim 1, wherein the casing comprises a viewing window.

11. The device of claim 1, wherein the ring comprises one or more cutaway regions.

12. The device of claim 1, wherein the ring comprises a biocompatible material selected from the group consisting of stainless steel, aluminum, titanium alloy, cobalt alloy, titanium ceramic, aluminum oxide, zirconia, silicone, and plastic.

13. The device of claim 3, wherein the hook, the graduated portion, and the countersink of the shaft are constructed from a single material.

14. The device of claim 3, wherein the hook, the graduated portion, and the countersink of the shaft are constructed from a composite of materials.

15. A method of determining a necessary length of a screw to be inserted into a bone during an orthopedic procedure, comprising:
   inserting the proximal end of the device of claim 1 into a predrilled hole into bone;
   observing a graduated marking of a graduated portion of the device of claim 1 through a window in the casing of the device; and
   determining a length of a screw based on an observed depth of the shaft inserted into the bone.

16. The method of claim 15, wherein the device comprises at least one graduation marking along the shaft where at least a portion of the shaft is visible from the outer surface of the casing, and wherein measuring the observed depth of the shaft within the bone comprises identifying a graduation marking visible within the window in the casing of the device.

17. The method of claim 15, wherein the length of the screw is equal to the observed depth of the shaft.

18. A method of forming a countersunk recess for a head of a screw using the device of claim 1, comprising:
   placing the countersink of the shaft in direct contact with a target site of a bone; and
   actuating the device to form a countersunk recess.

19. A method of preparing a bone for placement of a screw using the device of claim 3 comprising: 1) determining an appropriate hole depth and screw length using the hook and the graduated portion of the shaft; and 2) preparing a site of interest on a bone for a screw using the countersink of the shaft.

* * * * *